(12) United States Patent
Gallagher, Jr. et al.

(10) Patent No.: US 8,292,624 B2
(45) Date of Patent: Oct. 23, 2012

(54) ORAL APPLIANCE

(75) Inventors: John H. Gallagher, Jr., Haverford, PA (US); Roman Bielski, Coopersburg, PA (US)

(73) Assignee: Dent-Chew Brush LLC

( * ) Notice: Subject to any disclaimer, the term of this patent is extended or adjusted under 35 U.S.C. 154(b) by 11 days.

(21) Appl. No.: 12/504,942

(22) Filed: Jul. 17, 2009

(65) Prior Publication Data
US 2009/0277461 A1 Nov. 12, 2009

Related U.S. Application Data (63) Continuation-in-part of application No. 11/701,856, filed on Feb. 1, 2007, now abandoned.

(60) Provisional application No. 60/764,119, filed on Feb. 1, 2006.

(51) Int. Cl.
*A61C 15/00* (2006.01)

(52) U.S. Cl. .................................................. 433/216

(58) Field of Classification Search .................. 433/216, 433/6, 37; 128/861, 862
See application file for complete search history.

(56) References Cited

U.S. PATENT DOCUMENTS

| | | | |
|---|---|---|---|
| 2,257,709 A | | 10/1938 | Anderson |
| 3,769,652 A | * | 11/1973 | Rainer ........................ 15/167.2 |
| 4,011,616 A | | 3/1977 | Kennedy |
| 4,237,574 A | | 12/1980 | Kelly et al. |
| 5,175,901 A | | 1/1993 | Rabinowitz |
| 5,213,428 A | | 5/1993 | Salman |
| 5,419,916 A | * | 5/1995 | Yamamoto et al. ........... 424/456 |
| 5,620,011 A | | 4/1997 | Flowers |
| 5,970,981 A | * | 10/1999 | Ochel ........................ 128/859 |
| 6,280,767 B1 | | 8/2001 | Sano et al. |
| 7,404,403 B2 | | 7/2008 | Farrell |
| 2003/0205234 A1 | * | 11/2003 | Bardach et al. ............... 128/861 |
| 2005/0039280 A1 | | 2/2005 | Trimmer et al. |

OTHER PUBLICATIONS

Poly(Ethylene Glycol)-Modified Gelatin Nanoparticles for Intracellular Delivery, Kaul et al., Pharmaceutical Engineering, Sep./Oct. 2003, p. 1-5 (2003).
Phase Separation Coupled with Gelation in Polyethylene Glycol-Gelatin-Aqueous Buffer System, Nezu et al.. Bull. Chem. Soc. Jpn., 64, 1618-1622 (1991).
Peroral Route: An Opportunity for Protein and Peptide Drug Delivery, Sood et al., Chem. Rev., 101, 3275-3303 (2001).
Reviews—Biodegradable Polymers for protein and Peptide Drug Delivery, Gombotz et al., Bioconjugate Chem. 6, 332-351 (1995).
Emulsion Type New Vehicle for Soft Gelatin Capsule Available for Preclinical and Clinical Trials: Effects of PEG 6000 and PVP K30 on Phisiochemical Stability of New Vehicle, Amemiya et al., Chem. Pharm. Bull. 47(4) 492-497 (1999).

* cited by examiner

*Primary Examiner* — Sunil K Singh
(74) *Attorney, Agent, or Firm* — Duane Morris LLP (57) ABSTRACT

An oral appliance with opposite channels for receiving the upper and lower dental arches is made from an edible material, in particular a gel. The appliance is integrally molded with protrusions that act as brush bristles to clean the teeth and stimulate the gums when manipulated in a chewing motion. The gel composition is water soluble and degrades in saliva. After chewing on the appliance for a time to clean the teeth, the product becomes masticated, broken up and ingested. The appliance can incorporate a breath freshener or an active dental composition, or can be flavored or can incorporate a food supplement or pharmaceutical, in which case the appliance is intended to be chewed up and eaten after serving its tooth cleaning function. Dentifrice reservoirs, air passageways and lateral braces for manipulation by the tongue can be provided.

13 Claims, 4 Drawing Sheets

ORAL APPLIANCE

CROSS REFERENCE TO RELATED APPLICATIONS

This application is a continuation in part of application Ser. No. 11/701,856, filed Feb. 1, 2007 now abandoned, and claims the priority of provisional application Ser. No. 60/764,119, filed Feb. 1, 2006.

FIELD OF THE DISCLOSURE

This disclosure encompasses the fields of oral appliances, dental hygiene and consumable food products.

The disclosed oral appliance is composed of a digestible gel composition, molded as a double-arch trough that engages movably with a user's gums and teeth to stimulate and clean the gums and teeth during chewing movements, and optionally can incorporate one or more functional compositions that are released as the appliance breaks down under the influence of saliva and chewing. Oriented protrusions can be molded integrally with the arches, and serve to dislodge particles in a manner similar to the action of toothbrush bristles. The product is preferably integrally molded using a natural gel protein with nutritional value and can incorporate a flavor. The functional compositions likewise can comprise breath freshener, a pharmaceutical composition, food supplement, vitamin or other dental hygienic or consumable material.

RELATED ART

Protective mouth guards for sports generally comprise a channel shape with an arched structure that fits the wearers' dental arches. A bottom of the channel shape resides between the wearer's upper and lower teeth. Side walls of the channel reside along the inside and outside at least one of the upper and lower dental arches. The channel typically forms two opposite channels respectively engaging the upper and lower teeth. The upper and lower channels typically are joined as a single integral piece with channels opening in opposite directions, up and down, but also can be separate pieces.

The composition of a mouth guard is chosen to provide both cushioning and structural support for the jaw under the shock of blows to the face. Advantageously, a mouth guard conforms closely to the user's teeth, and may comprise a thermoplastic such as ethylene-vinyl acetate that is softened with heat and fit to the user's teeth. Alternatively, such a device can be made of a thermoset plastic. The device needs to be durable. It is intended to be re-used. An example is found in U.S. Pat. No. 7,404,403—Farrell.

Efforts have been made to adapt the arched channel structure of an athletic mouth guard to the function of a toothbrush that engages all the teeth at once. Examples are found in U.S. Pat. No. 2,257,709—Anderson; U.S. Pat. No. 3,769,652—Rainer; U.S. Pat. No. 4,011,616—Kennedy; U.S. Pat. No. 4,237,574—Kelly et al.; U.S. Pat. No. 5,175,901—Rabinowitz; and published application US 2005/00038280—Trimmer et al. Chewing motions move the teeth relative to the device. A chewing-driven toothbrush device as disclosed can include embedded toothbrush bristles of a dissimilar material, supplies of dentifrice that are carried by or introduced into the tooth-receiving channels, tubing for coupling a water supply to flush the mouth, and vibrating devices that cause the arched channel to move relative to the user's teeth. These devices have not achieved wide acceptance.

Chewing-driven toothbrushes also are intended to be re-used. U.S. Pat. No. 5,213,428—Salman discloses a tooth cleaning device comprising a finger tube with outward surface projections forming bristles. The user places the device on an index finger, and with the clad index finger placed into his or her mouth, rubs the bristles over the teeth and gums. This device is disposable, and according to the disclosure is composed of a biodegradable plastic so as to decompose under the action of microorganisms.

A material may be designated as "plastic" because it is deformable, but usually the term refers to a high molecular weight thermoplastic or thermosetting polymer, typically based on petroleum. Plastic compositions that are "biodegradable" are compositions that can be broken down by bacteria or other microorganisms in a landfill or the like, when discarded after use. A composition considered biodegradable may be unfit to be eaten by humans. On the other hand, routine foods typically can be consumed by microorganisms and will rot away if discarded in a compost or landfill. The point is that the concepts of biodegradability and edibility are not coextensive.

It is known to package pharmaceutical compositions in gel capsules that are intended to be consumed. Gel capsules may have a soft gel or a hard gel and typically are intended to be swallowed intact, in which case the gel material enveloping the payload is breached in the stomach to release the capsule contents. A gel capsule also might be held in the mouth to be dissolved by saliva, or bitten to release contents. These capsule lack a functional structure apart from forming an envelope around the contents.

It is known to provide arbitrarily shaped food products that incorporate a soft gel, for example as the so-called "gummy" gel candies. Embodiments are known that incorporate vitamins. There is no relationship between the structure of the product and dentition of the person who consumes it.

Polymeric compounds that have been used in oral applications (i.e., orally consumable products), include the following types of macromolecules: (1) polymers of natural origin and their copolymers (e.g., polysaccharides (cellulose, hyaluronic acid, β-glucans and emulsans); proteins and peptides (collagen, gelatin, albumin, alginate)); (2) modified natural polymers and copolymers (e.g., chitosan, trimethylated chitosan, carboxymethyl chitosan/polyisopropylacryl-amide, hyaluronic acid ester); (3) synthetic polymers and copolymers (e.g., poly(methyl methacrylate), poly(acrylic acid), esters of poly(lactic and glycolic acids), polyethylene glycols, poly(vinyl alcohol)), substituted poly(methacrylamide), poly(vinylpyrrolidone), poly(amino acids) such as trimethylated poly-(glutamic acid), poly(cyanoacrylates), poly(alkyl cyanoacrylate), poly(methacrylic acid-g-ethylene glycol), poly(ethylene oxide) with montmorillonite, polyvinyl methyl ether/maleic acid); and (4) mixtures of copolymers of natural and synthetic origin (e.g., copolymers of acrylamide and xanthan). The majority of these polymers cannot be easily molded, but can be incorporated into a mold. Polymers that can be molded and thus applicable for use as a molded oral appliance include polyacrylates and polymethacrylates, poly(ethylene glycols), and poly(propylene glycols).

It would be desirable to have a shaped oral appliance containing materials that are water soluble, edible and likewise biodegradable by microbial action. Polymeric materials useful for incorporation in the appliance should belong to the GRAS category (generally recognized as safe); should hold a functional shape when molded, including with respect to finely detailed structural aspects; should be stable both chemically and physically under typical storage conditions for at least several weeks; should exhibit appropriate physical properties such as transition temperature (i.e., the transition temperature should not be too low), possess appropriate viscosity, water adsorption, ease of creating the designed shape, etc., as well as exhibit appropriate chemical properties such as biodegradability under selected conditions, lack of monomers in the macromolecular structure, compatibility with selected additives and compounds to be released as the product is consumed, desired water solubility, ease of crosslinking if required, etc.

The rate of dissolution of the product in saliva during chewing should be such that the materials degrade within a few minutes, and the materials should be at least in some extent soluble in saliva (water) and/or biodegradable either in water or in the presence of relevant enzymes such as hydroxylases.

Gelatin (e.g., derived from bovine or porcine skin, carrageenan or other "elasticity carrying" protein), has been used together with poly(ethylene glycol) (PEG) in a variety of applications, e.g., PEG has been covalently attached to specific functional groups (i.e., amino of gelatin); phase separation and gelation of mixtures containing gelatin and PEG have also been studied. Such phase separation often takes place in multi-component polymer solutions due to mutual incompatibility or due to their different interactions with the solvent such as water. As disclosed in U.S. Pat. No. 5,419,916, succinated gelatin (presumably crosslinked with succinic anhydride) has also been used together with PEG to form a hard capsule.

U.S. Pat. No. 6,280,767 teaches the formulation of a chewable soft gelatin capsule. The reference discloses the use of gelatin, a mixture of "plasticizers," and (water-insoluble) cellulose. The plasticizer mixture is composed of (a) glycerol, (b) PEG or PPG (polypropylene glycol) and (c) a material such as a sugar or sorbitol. It would be desirable for an oral appliance not to contain glycerol and sugars.

SUMMARY

What is needed is an appliance that cleans teeth by contact between the relatively movable surfaces of the teeth and a structure configured for tooth cleaning and gum stimulation, that optionally can release a composition for desired effect of a cleansing, fragrant, food supplementing or other nature, and is simply positioned on the teeth, chewed to achieve its effects, and moreover, is eaten as an ingestible item when the tooth cleaning process has been completed. These aspects are provided in part by an arched channel dental appliance molded substantially integrally as an edible gel, with the aspects described in detail herein.

To serve the foregoing objects, a composition, structure and technique are needed whereby a gel material is caused to hold the structure of a chewing-style tooth cleaner, in particular an arched-trough chewing-action tooth brush or similar appliance, wherein the gel material is an edible food product and the product is consumed, i.e., chewed and eaten, as a part of its character and appeal. In addition to the embodiments wherein the appliance is a chewing-action tooth brush, alternative embodiments can include, among other products, mouth guards, orthodontic appliances, dental appliances or devices for application of an active dental composition such as tooth whitener or fluoride treatment, anti-snoring jaw position fixation appliances and similar devices that embody a structure with a predetermined structural relationship to the mouth, and can be composed of a material comprising an ingestible gel.

A gel composition is needed with a formulation characterized by particular attributes and a fixed structure that serves the functions described. According to the present disclosure, a user can chew upon a tooth brushing arch appliance having bristle-like protrusions molded integrally with one another as a gel composition. The gel compositions that are disclosed have sufficient integrity to last for a time while movement of the protrusions over the teeth and gums cleans the teeth and gums. Moreover, the compositions are degradable with mastication and with the action of saliva so as to be consumed (eaten) as the chewing action continues. The disclosed product, generally comprising a functionally rigid dental arch product with integrally molded bristles and other features, comprises or consists essentially of an edible gel food composition that breaks down as the entire appliance is masticated, broken into pieces and swallowed, i.e., chewed up and eaten by its user.

In one embodiment, the disclosed product comprises an oral appliance with a structure similar to that of a mouth guard. Preferably, two oppositely facing channels respectively follow the maxillary and mandibular arches and receive the teeth when placed in the user's mouth. In addition, the product is shaped for the functions of tooth brushing and cleaning the teeth and stimulation of the gums, tongue, etc., including removing plaque at the gingival margin. Compositions that can be incorporated in the molded product include breath freshener, flavoring, vitamins, or dietary supplements, pharmacological compositions and/or other similar component materials that are advantageously either deployed in the mouth or ingested, wherein such materials and can be molded homogenously with or incorporated by injection or otherwise into voids or cavities in a molded product that is molded to a shape that serves the desired function, e.g., a double-arched channel with inward protrusions that operate as bristles to dislodge material in and on the teeth, gums and/or tongue.

According to one embodiment, as to composition the oral appliance comprises a formulation including: (1) gelatin; (2) a water soluble polymer such as a polyether, a water soluble polyester, or a water soluble polymer that is formed as a result of polymerization of acrylic acid or acrylamide or their derivatives; and (3) water.

According to one embodiment as to molded structure, the user is able with the appliance in the mouth to brush or stimulate all three exposed surfaces of the teeth of the upper and lower bite, the gingival margin, and the surface of the tongue. Chewing the appliance produces clean teeth and freshened breath, comparable to the results of traditional brushing with an elongated handle toothbrush, enabling maintenance of oral hygiene without the need for running water, as a single use convenience item or as an item in a military ration pack that obviates the need to carry a brush and a supply of dentifrice. This item is not only disposable in the sense of being water soluble and biodegradable, but moreover is advantageously ingested by the end user to conclude the tooth cleaning process.

DETAILED DESCRIPTION

In one embodiment, the invention comprises an oral appliance as shown in FIGS. 1 through 7, composed and configured as a one-time use disposable full mouth tooth cleaner operated by a chewing motion. For this purpose, the appliance is formed with upper and lower bite channels having inwardly disposed protrusions that operate as bristles for cleaning the teeth and stimulating the gums. Preferably, the whole appliance including the protrusions that operate as bristles, are integrally molded in one piece, of an edible composition based on an ingestible gel, optionally including supplemental components such as breath freshener, flavoring, or compositions with a cosmetic, oral therapeutic or generally pharmacological function that are intended for oral dosing or at least are safely ingestible.

The general shape of the appliance resembles that of an athletic mouth guard, having two channels following the dental arches, disposed opposite from one another so that the respective upper and lower channels accept the teeth of the maxillary arch 2 and mandibular arch 4. Although the absolute orientation of the human user is arbitrary, these arches 2, 4 are sometimes referred to as the "upper bite channel" 2 and the "lower bite channel" 4 or as the "upper and lower bite channels."

The bite channels of the oral appliance generally match the dental arches and can be provided in small, medium and large sizes. The appliance can be somewhat resiliently deformable to enable it to match and receive the dental arches. When the device is placed in the oral cavity such that the user can bite down on the device, the vertical crown surfaces of all the teeth and their cusps preferably are in substantial contact with the interior surfaces of the upper and lower bite channels 2, 4.

In the exemplary embodiment shown, the upper and lower bite channels, although relatively inverted, are separated by and attached to, a dentifrice reservoir 3 that is divided horizontally to create an upper dentifrice reservoir 8 and a lower dentifrice reservoir 9, of substantially equal size and volume. Located on the horizontal surfaces of both the upper and lower bite chambers that are common to the respective upper and lower dentifrice reservoirs are apertures 10 that permit the passage of the dentifrice from the adjacent dentifrice reservoir into the bite chambers upon the reservoirs compression. The device when placed in the mouth is chewed on, causing relative displacement of the appliance and the teeth.

Figure 8:
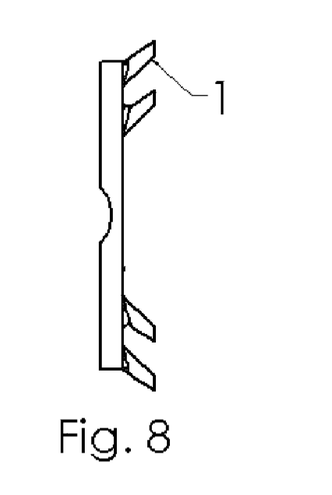
FIG. 8 is a vertical view depicting the angular protrusions according to one embodiment.

The interior surfaces of the bite channels are lined with closely spaced protrusions 1 that form brush bristles and can vary in length, angle and thickness. In one example, bristles are set at varying angles such that they engage at 45°, 90° and 135° relative to a tooth surface or engaged at about 40 to 45° off vertical in the direction of the gum line and 5 to 10 degrees off horizontal directed to the forward position of the mouth on all bristles beyond the canine. One embodiment of inclined protrusions or bristles is shown in FIG. 8. Relatively longer protruding brush bristles that reach into the interproximal regions of the oral cavity (between adjacent teeth) serve to cleanse and remove hard to reach food particles. This same type of brush bristle or protrusion, when positioned directly on the surface of a tooth, provides a broader sweeping action as a result of its deflection. Shorter protrusions when occupying interproximal regions aid in agitating the dentifrice and/or such saliva as is present, to enhance the dislodging of food particles and when positioned directly on the tooth's surface provides the desired brushing of both the tooth and the gingival margin to remove plaque.

Figure 9:
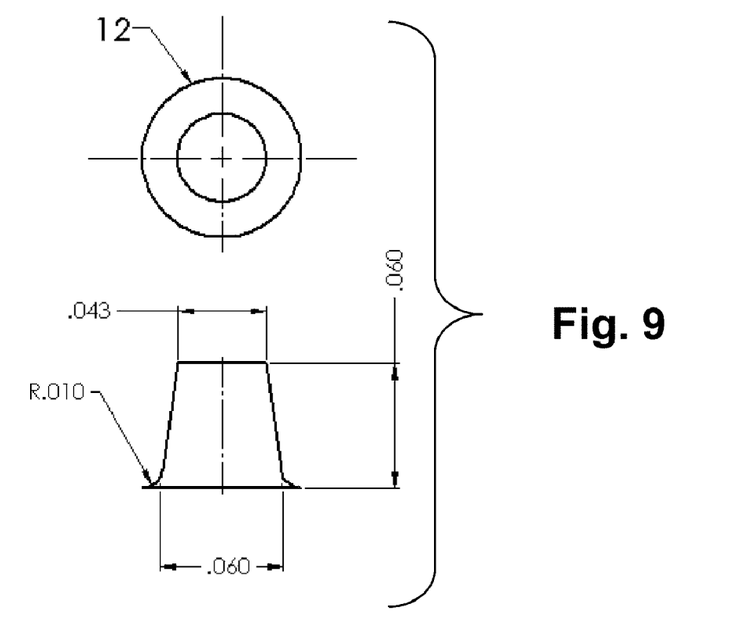
FIG. 9 is a mechanical illustration of a short protrusion from the end and side, according to one embodiment.
Figure 10:
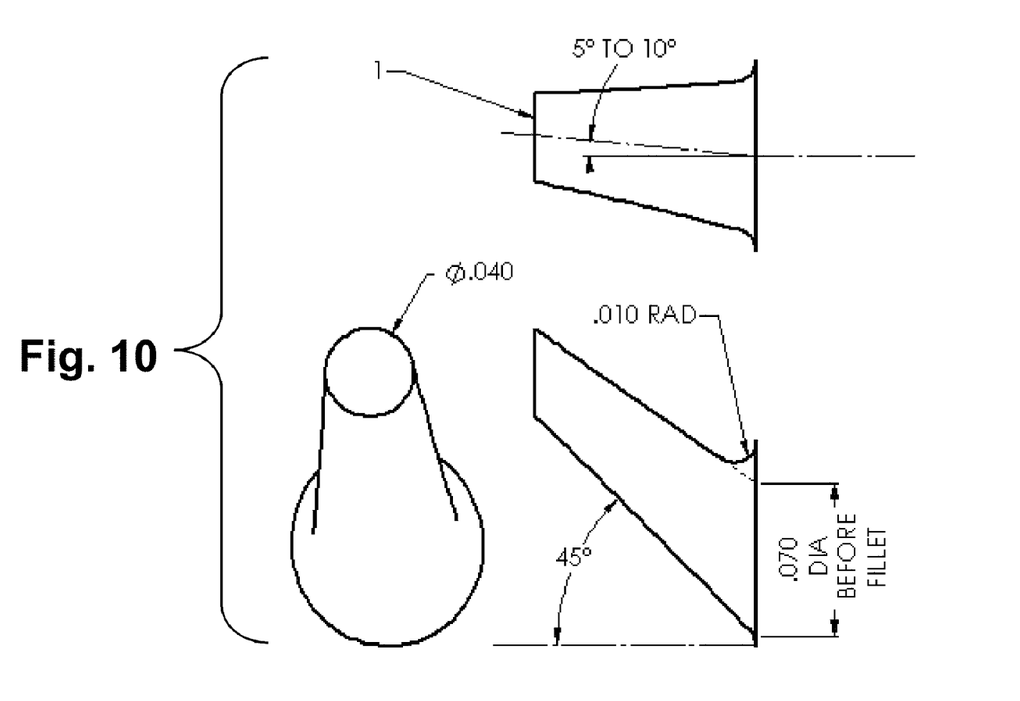
FIG. 10 is a mechanical illustration of a longer protrusion shown inclined in orthogonal axes.

In one embodiment shown in FIG. 9, the diameter of the bristles 1 is approximately 60 mil (0.060") at the connection to the interior channels of the upper and lower bite encircled by an elliptical fillet and extending to a tapered end having a diameter of ≈40 mil (0.040"). Bristles on the horizontal interior surface of both the upper and lower bites 12 and the palate brace 6 are ≈60 mil (0.060") at the connection encircled by an elliptical fillet and extending to a tapered end having a diameter ≈43 mil (0.043") extending to a height ≈60 mil (0.060"). The length of these bristles may vary but in general can have a length of 1.5 mm to 3 mm and a maximum taper to an extreme end of not less than three mils and a length not less than forty mils. FIG. 10 shows a bristle/protrusion with an incline and a taper in mutually perpendicular directions. In a preferred embodiment, the protrusions forming the bristles are integrally molded in one piece with the channels, of the same material comprising an ingestible gel as described more fully below.

Figure 2:
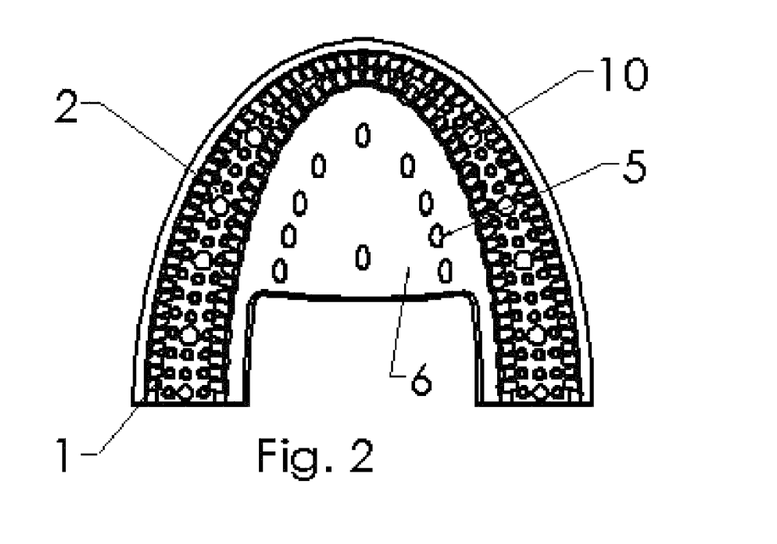
FIG. 2 is a plan view of the appliance showing material ports throughout the maxillary arch and vacuum release ports positioned randomly throughout the palate brace.
Figure 3:
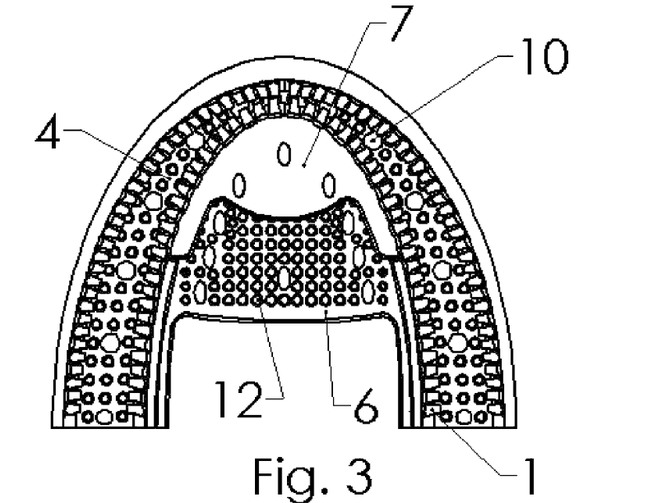
FIG. 3 is a reflective plan view illustrating the mandibular arch revealing the lingual brace and the exposed portion of the palate brace.
Figure 4:
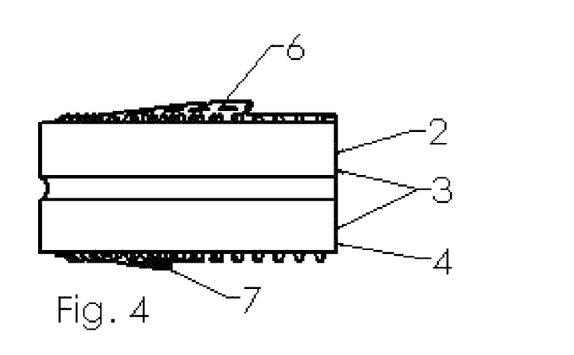
FIG. 4 is a side elevation view of the appliance.

In one embodiment, a palate brace spans the roof of the mouth as shown in FIG. 2, being connected to the uppermost edge of the interior wall of the upper bite channel. The palate brace is resiliently deformable and conforms to the roof of the mouth along approximately a lateral line generally extending between the first molars opposite from one another on the maxillary arch. The palate brace has two distinct functions. The palate brace is configured to present closely spaced brush protrusions as seen in FIG. 3, which can be of multiple lengths and disposed at differing angles to provide an irregular surface on which to scrub the papillae of the tongue. The palate brace 6 also can be engaged by the tongue to position and to stabilize the oral appliance while carrying on a chewing motion wherein the teeth are alternately pressed into the arched channels toward the bottom and lifted relative to the bottom of the respective channels. This causes the protruding bristles to scrub at and between the teeth and over the surfaces of the teeth and gums to cleanse the teeth and stimulate the gums.

Applying tongue pressure on the palate brace presses the appliance against the roof of the mouth, holding it in place while displacing the lower jaw and applying the brushing action to the teeth and gums in the lower jaw. Relieving tongue pressure on the palate brace allows the appliance to become displaced, at least somewhat, together with the lower jaw, applying brushing action to the upper teeth and gums. One or more vacuum vent ports 5 is placed to form an aperture through the palate brace as seen in FIGS. 1 and 2, such that the appliance does not resist displacement due to vacuum engagement with the upper jaw.

The lower bite channel 4 is spanned by a lingual brace from its corresponding lower edge on a lateral line that approximately intersects with the interproximal area between the 1st and 2nd premolar (bicuspid 21-20) on one side and the 1st and 2nd premolar (bicuspid 28-29) on the opposite side. When the upper bite is to be cleansed the tongue is depressed against the lingual brace 7, visible vertically in FIGS. 4 and 5, which holds the oral appliance in place against the lower bite, or alternatively permitted to become displaced when tongue pressure is relieved. A steady chewing motion with some control using the tongue as described, serves to clean the upper and lower bites as the teeth and the gingival margins of the arches move in and out of the bite channels.

The appliance consists essentially of an ingestible gel composition. While the appliance is being chewed upon, thereby moving the bristle protrusions over the teeth and gums, the teeth of the maxillary and mandibular arches are moved toward and away from one another and also in a grinding motion in a plane whereby the lower jaw moved forward and back and laterally from side to side, relative to the upper jaw. This motion brushes the cusp surfaces of both the upper and lower bites, the lateral sides of the teeth and the gingival margins, and initially also in the spaces between the teeth where the bristle protrusions reach. At the same time, the appliance is subjected during this chewing motion to the action of saliva. Mastication and saliva cause the surface of the appliance to erode, and the whole appliance to break into pieces. When broken down, eventually into comfortably small pieces, the user simply swallows the pieces that thus disposes of the appliance. Users who are not so inclined may discard the appliance after a time, whereupon the discarded appliance likewise breaks down with the action of microorganisms.

Figure 1:
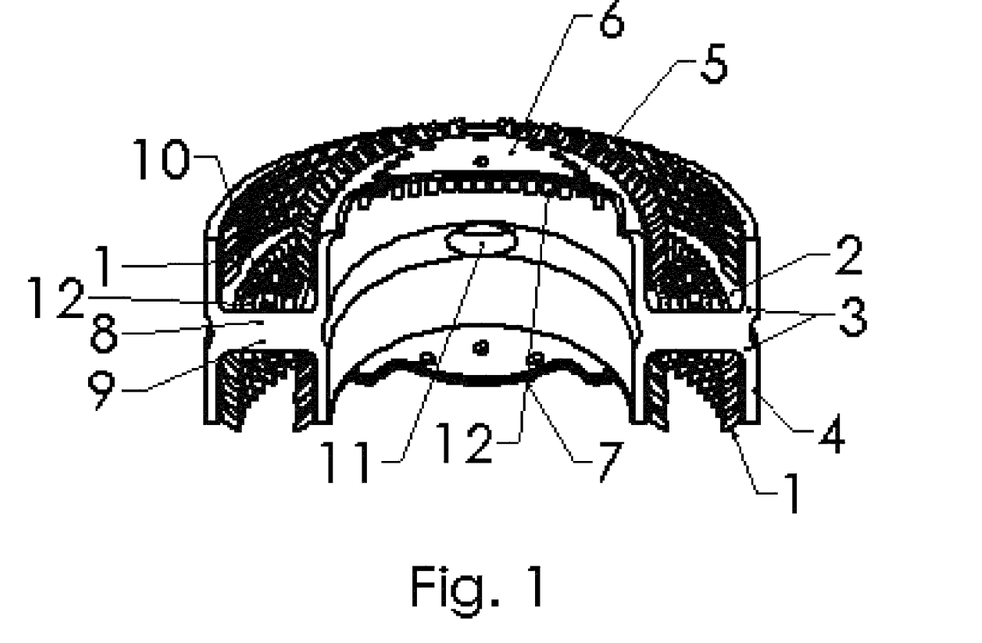
FIG. 1 is a perspective posterior view of the appliance, i.e., as it would be seen by the user inserting into the mouth.
Figure 5:
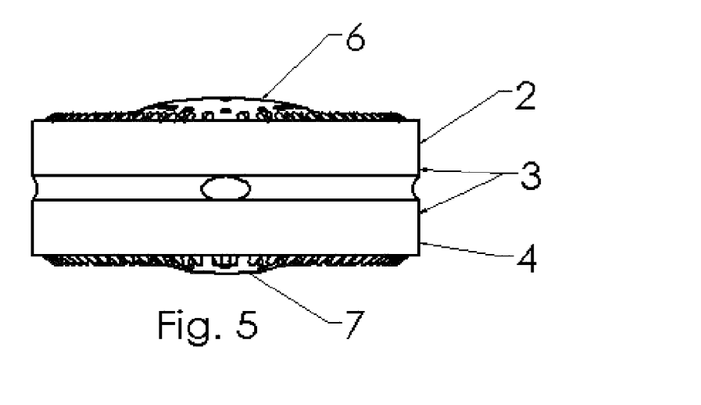
FIG. 5 is a front elevation view of the appliance.
Figure 6:
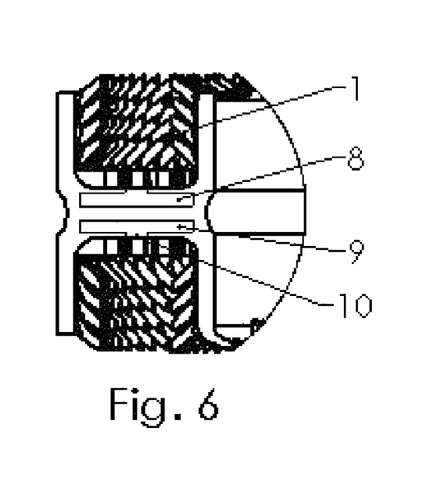
FIG. 6 is a view of a cross-section of the appliance taken from the buccal portion of the maxillary and mandibular arches.
Figure 7:
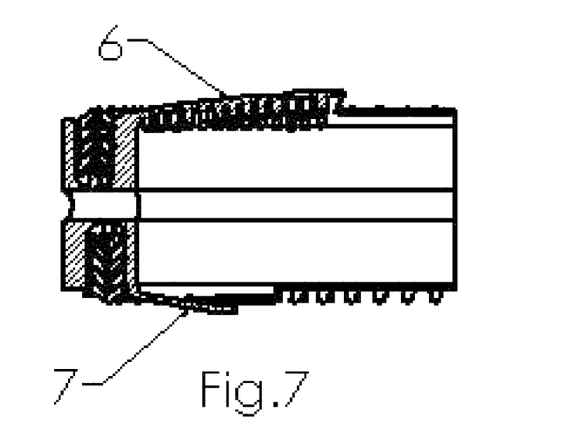
FIG. 7 is a view of the cross-section of the appliance taken from the facial portion of the maxillary and mandibular arches in areas other than that of the facial centerline where the inhalation port is located.

A breathing port 11 as seen in FIGS. 1 and 5 provides an opening through the upper and lower dentifrice reservoir at the facial centerline of the maxillary and the lingual arches, permitting the user to breathe through the mouth notwithstanding the presence of the appliance.

In a preferred arrangement, the appliance is monolithic and manufactured of the same substance comprised primarily of a gelatin compound with high bloom strength in excess of 150 grams. The materials formulation enables the disposable unit to be both water soluble and biodegradable. In one embodiment, the oral appliance comprises a formulation including: (1) gelatin (derived from e.g., bovine or porcine skin, carrageenan or other "elasticity carrying" protein); (2) a water soluble polymer such as a polyether, e.g., a poly(ethylene glycol) and poly(propylene glycol), a water soluble polyester, e.g. those derived from lactic and glycolic acid, a water soluble polymer formed as a result of polymerization of acrylic acid or acrylamide or their derivatives, e.g., methacrylic acid, methacrylamide or poly(vinylpyrrolidone); and (3) water. In a preferred embodiment, the water soluble polymer is dissolved in water with stirring and heating if needed, and the solution is then treated so as to impart the desired level of elasticity, introducing a protein such as gelatin. The mixture is allowed to swell for several minutes at ambient temperature, heated up to the boiling point of water (at normal pressure) and vigorously stirred.

In the manufacture of the present invention, PEG 400 (amounts up to 1000 should be effective) (8 units of mass) and PEG 4000 (or 1000, 2000 or 6000) (from 0 to 2 units of mass, preferably 1 unit of mass) are dissolved in water (about 25 to 30 units of mass; e.g., between 15 and 50). Next, gelatin (various types are applicable, 7 to 15 units of mass, preferably 10) is added to the mix. After the swelling is over (about 10 minutes; can be up to about 24 hours) the mixture is stirred while heated to 50-100° C. (preferably 70-80° C.). The resulting solution is introduced (i.e., injected) into the mold and cooled to the ambient temperature).

Various additives may also be included in the mixture. If such additives are water soluble, they should be added together with the polyethylene or polypropylene glycol. Conversely, if the additives are water insoluble they can be introduced with gelatin. In accordance with the present invention, the product can be constantly stirred if a uniform distribution of the additive is desired, or the product can be left to settle if it is desired that the additive settle close to one side of the polymeric mold.

Suitable additives include: fluoride anion, xylitol, chlorhexidine, water soluble vitamins (such as B and C) and water insoluble vitamins (such as A and E), various nutraceuticals, minerals, medicines, etc. The formulation may also contain components affecting taste, such as sweeteners (e.g., sucrose, glucose, saccharin, aspartame, Splenda®, etc), citric acid, fruit extracts, and preservatives such as sodium benzoate, citric acid derivatives, etc.

In accordance with the present invention, the gelatin is not covalently bonded to PEG. The compositions are such that there is no phase separation; the ratios leading to two phases were rejected. Furthermore, gelatin and PEG are uniformly distributed throughout the product, and the gelatin is not crosslinked. The formulations of the present invention differ from the prior art in that the present invention does not employ glycerol and sugars, and in a preferred embodiment, the present invention employs more than 100 parts of gelatin for 100 parts of PEG. Examples 1 and 2 below describe exemplary molding procedures that may be used in the manufacture of the invention.

EXAMPLE 1

PEG 4000 (1.2 g) and PEG 400 (8.4 g) were dissolved (at slightly elevated temperature) in water (34.0 g). Gelatin (coarse, 175 Bloom ("Bloom" value—firmness or strength of the set gel); 9.9 g) was added at once to the solution at room temperature. After the swelling was complete (a few minutes) the mixture was thoroughly stirred when heated to about 80° C. (about 10 minutes) to form a single phase. The mixture was then cooled to produce about 47 g of the hard and elastic material.

EXAMPLE 2

Gelatin (coarse, 275 Bloom; 9.9 g) was added at once to water (38.4 g) containing dissolved PEG 400 (9.8 g). The mixture was left at room temperature to swell (about 5 minutes; not all the liquid was absorbed). The mixture was heated to about 70-80° C. with constant stirring. A non-homogeneous, two phase mixture was formed, which eventually (about 5-10 minutes of stirring) at 75° C. became homogeneous. The resulting material (after cooling) is whitish, soft and highly elastic, and maintains its shape well.

EXAMPLE 3

Control

Gelatin (175 Bloom; 9.8 g) was added at once to water (32.0 g) and the mixture was left to swell. After about 5 minutes the mixture was heated (to about 70° C.) during stirring. The product (after cooling it is a single phase) is clearly softer than the products from experiments in which some PEG was added. A product exhibiting a thickness of even a few millimeters can be impaired. Furthermore, after a few weeks the product was degraded by fungi. In contrast, PEG-containing products exhibit much better mechanical properties (e.g., superior strength and hardness of resulting product), and appear to have a lower tendency to support the growth of microorganisms.

In further testing of the present invention, the following experiments were performed: PEG 400 and another polymer (designated A, B, C or D) were each mixed at room temperature with the selected amount of water. Next, the gelatin was added to each mixture, briefly stirred and left to swell for about 10 minutes (see Table 1 below). The mixtures were then heated with stirring to about 80° C. and left to cool down to ambient temperature. Each product's mechanical strength and texture was then evaluated.

TABLE I

| PEG and Polymer Combinations | | | | |
| --- | --- | --- | --- | --- |
| Compound | Experiment 1 | Experiment 2 | Experiment 3 | Experiment 4 |
| PEG 400 | 4.0 g | 4.0 g | 4.0 g | 4.0 g |
| Polymer | A (1.0 g) | B (0.50 g) | C (1.1 g) | D (0.7 g) |
| Water | 18.2 g | 24.0 g | 21.0 g | 20.5 g |
| Gelatin, coarse 275 Bloom | 5.0 g | 5.5 g | 7.5 g | 5.1 g |

A: Starch, hydroxyethylated, from Polysciences, Inc.
B: Polyacrylic acid, from Sigma-Aldrich ® (MW = 4,000,000)
C: Polyvinylpyrrolidone, from Polysciences, Inc. (MW = 40,000)
D: Polyacrylamide, from Sigma-Aldrich ® (MW = 200,000)

Products from experiments 1, 3, and 4 exhibited particularly good mechanical properties, while the result of experiment 2 gave an acceptable product.

The foregoing chemical composition is totally ingestible, biodegradable, water soluble and subject to breakdown in the mouth with mastication and latent enzymes that are found in saliva. The integrally molded product has a stable molded shape and structural rigidity "on the shelf" before it is used. When placed in the mouth, the product engages the teeth and gums, applying the integrally molded bristle protrusions against the teeth and gums. The product shape and the active application of the bristle protrusions to the teeth and gums endures for a time during which chewing on the product causes the integrally molded bristle protrusions to scrub over the teeth and gums. After this brief time (e.g., up to one to two minutes depending on the vigor with which the product is chewed upon by the user), the integrity of the product breaks down. Mastication breaks the product up. The product is intended to be further masticated and eaten, particular if an active composition is included such as a food supplement or pharmacological dosing.

On the other hand, a user may prefer to spit out and discard the product after chewing on it for a time to clean the teeth. The gel material by then is infused with saliva and is structurally deteriorated. Moreover, the gel material is not only susceptible to latent enzymes from saliva, but is a foodstuff for bacteria, fungi, insects and microorganisms, rendering the material biodegradable.

Although the protrusions or bristles facing the teeth and gums, and optionally the tongue on one or more transverse braces, in another embodiment the bristles are formed as elongated tapering forms that resemble the bristles of a brush while protruding inward integrally with the channel walls. Those bristles attached to the vertical interior walls preferably are set at a compound angle: 40 to 45 degrees off vertical in the direction of the gum line (i.e., upwardly in the upper channel and downwardly in the lower channel) and 5 to 10 degrees anteriorly (toward the front teeth) on all bristles beyond the canine. The bristle rows that are positioned to first come into contact with the gingival margin are designed to deflect in the direction of their 5 to 10 degrees anteriorly, to enhance cleaning at the intersection of the tooth surface and the gum line.

The protrusions on the surfaces of the channels and braces can be relatively more or less thin and elongated, but preferably complement the interproximal spaces, the contours and edges of the teeth, and the gingival margins. The protrusions function like the bristles of a toothbrush. The protrusions or bristles optionally can be oriented to achieve certain results. In the embodiment described above, protrusions on the channel side walls are inclined toward the gum line (apically). It is also possible to provide at least some protrusions on the channel side walls that are inclined in a coronal direction (towards the crown of the teeth), so that particles on or between the teeth are hooked and pushed away from the gums during chewing and relative displacement of the appliance versus the teeth. A coronal bristle orientation may tend to bias movement of the appliance in the direction of the gums.

Bristle protrusions can be inclined in distal (anterior) or mesial (posterior) directions, or in combinations (e.g., diagonally). For simplicity in molding, protrusions can generally define truncated conical forms with radiused fillet transitions, oriented perpendicular to the surfaces from which they protrude or being inclined as described. Under the actions of saliva and chewing, the protrusions become softened and deformed. Protrusions that are engaged by the cusps of the teeth can be sheared off.

The palate brace is used to lock the appliance into the upper bite when pressure is applied by the tongue to the roof of the mouth to enable brushing of the lower bite. The palate brace is also lined with bristles so the user may brush the dorsum tongue. The lingual brace is used to lock the appliance in place on the lower bite to enable brushing of the upper bite when chewing.

In another embodiment, four reservoirs dispense dentifrice equally into the upper and lower bites (not into the oral cavity and not for the purpose of taste) with equal measure to both sides of the respective bites. This arrangement is such that missing teeth have less effect in disproportional dispersion of the dentifrice Openings are provided, penetrating through the lingual brace and the palate brace, to relieve vacuum adhesion to the roof or lingual areas of the mouth. Pressure exerted by the tongue on one or the other of the palate brace and the lingual brace can either stabilize or help to manipulate the appliance during chewing, to achieve relative movement of the appliance and the teeth of both the upper and lower arches A passageway for air also is provided to enable respiration through the mouth when using the device. The passageway can be located between the upper and lower bites and centered at the front. This passageway improves comfort in particular for users who are suffering from nasal congestion.

Although the gel material is preferably integral and can comprise a mixture of ethylene glycol and gelatin, the material also can incorporate additives such as pharmacological compositions, food supplements, or the like, dispersed in the composition at the time of molding or injected into or applied to the surface of the material after molding. A self contained dentifrice preferably is provided in the dentifrice reservoirs as discussed. In one example, the dentifrice is composed of an antimicrobial mouth rinse, Xylitol, micro-abrasives and cleansing agents to clean the oral cavity and to balance or buffer the Ph level.

Additional embodiments and improvements within the scope of the invention will be apparent to persons skilled in the art in light of this disclosure. The invention has been disclosed in connection with a number of embodiments that are exemplary. The scope of the invention is not limited to the embodiments disclosed as examples and must be determined from the appended claims.

What is claimed is:

1. An oral appliance comprising:
   two inverted channels dimensioned to receive upper and lower bites of dental arches of a user, the channels being integral with one another and comprising a molded gel material that is edible and is configured to be broken up and ingested after a period of mastication;
   protrusions integral with the channels and bearing inwardly against teeth and gums of the user, wherein the channels and protrusions are configured such that mastication produces relative brushing movement of the protrusions over the teeth and gums;
   further comprising at least one lateral brace connecting lateral sides of at least one of the channels, wherein the lateral brace is placed such that pressure from a tongue of the user in a direction toward one of the bites during said mastication holds the oral appliance in place against said one of the bites, while the protrusions brush over the other of the bites; and,
   wherein the gel material consists essentially of (a) a mixture of gelatin and polyethylene glycol (PEG), and (b) has more than 100 parts of gelatin for 100 parts of PEG.

2. The oral appliance of claim 1, wherein the appliance is monolithic in that the channels and protrusions of the appliance are integrally and monolithically molded in the gel material.

3. The oral appliance of claim 1, further comprising a supplemental material incorporated into the appliance with the gel material, wherein the supplemental material is chosen from the group consisting of breath freshener, active dental composition, flavoring, a food or food supplement and a pharmacological composition.

4. The oral appliance of claim 3, wherein the supplemental material is water soluble.

5. The oral appliance of claim 1, wherein the gelatin and PEG are uniformly distributed throughout the gel material.

6. The oral appliance of claim 1, wherein the lateral brace comprises a palate brace extending between lateral sides of a maxillary one of the channels receiving the upper dental arch of the user, the brace being above the user's tongue, wherein the appliance is configured such that upward pressure of the tongue on the palate brace holds the appliance on the upper bite, permitting relative brushing movement with the lower bite, and further comprising protrusions on an underside of the palate brace directed toward the tongue.

7. The oral appliance of claim 1, wherein the lateral brace comprises a lingual brace extending between lateral sides of a mandibular one of the channels receiving the lower dental arch of the user, the brace being under the user's tongue, wherein the appliance is configured such that downward pressure of the tongue on the lingual brace holds the appliance on the lower bite, permitting relative brushing movement with the upper bite.

8. An oral appliance comprising:
   two inverted channels dimensioned to receive upper and lower bites of dental arches of a user, the channels being integral with one another of a monolithic gel material that is edible and is configured to be broken up and ingested after a period of mastication;
   protrusions molded integrally with the channels and bearing inwardly against teeth and gums of the user, wherein the channels and protrusions are configured such that mastication produces relative brushing movement of the protrusions over the teeth and gums;
   further comprising at least one lateral brace connecting lateral sides of at least one of the channels, wherein the lateral brace is placed such that pressure from a tongue of the user in a direction toward one of the bites during said mastication holds the oral appliance in place against said one of the bites, while the protrusions brush over the other of the bites; and,
   wherein the gel material comprises a formulation including: gelatin; a water soluble polymer; and water.

9. The oral appliance of claim 8, wherein the water soluble polymer comprises at least one of a polyether and a water soluble polyester.

10. The oral appliance of claim 8, wherein the water soluble polymer comprises a polymerization product of at least one of an acrylic acid, an acrylamide and a derivative of one of an acrylic acid and an acrylamide.

11. The oral appliance of claim 9, wherein the water soluble polyester is derived from at least one of lactic acid and glycolic acid.

12. The oral appliance of claim 10, wherein the derivative of one of an acrylic acid and an acrylamide is at least one of methacrylic acid, methacrylamide and poly(vinylpyrrolidone).

13. An oral appliance consisting essentially of a monolithic integrally molded gel material dimensioned for oral use, having surface protrusions arranged for relative movement over teeth and gums during mastication, wherein the appliance is formulated and configured to be ingested after a period of mastication during which the teeth are cleaned, and further includes a supplemental material incorporated into the appliance with the gel material, wherein the supplemental material is chosen from the group consisting of breath freshener, active dental composition, flavoring, a food or food supplement and a pharmacological composition, and wherein the gel material consists essentially of (a) a mixture of gelatin and polyethylene glycol (PEG), and (b) has more than 100 parts of gelatin for 100 parts of PEG.

* * * * *